United States Patent
Harrod et al.

(10) Patent No.: US 11,259,188 B2
(45) Date of Patent: Feb. 22, 2022

(54) ACCESS POINT WITH LIFE-CRITICAL NETWORK AWARE IEEE 802.11 CHANNEL SELECTION

(71) Applicant: KONINKLIJKE PHILIPS N.V., Eindhoven (NL)

(72) Inventors: John Price Harrod, North Andover, MA (US); Delroy Smith, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 200 days.

(21) Appl. No.: 16/495,208

(22) PCT Filed: Mar. 12, 2018

(86) PCT No.: PCT/EP2018/055994
§ 371 (c)(1),
(2) Date: Sep. 18, 2019

(87) PCT Pub. No.: WO2018/172108
PCT Pub. Date: Sep. 27, 2018

(65) Prior Publication Data
US 2020/0021996 A1   Jan. 16, 2020

Related U.S. Application Data

(60) Provisional application No. 62/474,212, filed on Mar. 21, 2017.

(51) Int. Cl.
*H04W 16/10* (2009.01)
*A61B 5/00* (2006.01)
(Continued)

(52) U.S. Cl.
CPC .............. *H04W 16/10* (2013.01); *A61B 5/00* (2013.01); *H04W 24/10* (2013.01); *H04W 72/0453* (2013.01); *H04W 84/12* (2013.01)

(58) Field of Classification Search
CPC . H04W 16/10; H04W 24/10; H04W 72/0453; H04W 84/12; A61B 5/00; H04L 29/08558
See application file for complete search history.

(56) References Cited

U.S. PATENT DOCUMENTS 8,428,036 B2   4/2013   Herscovici et al.
8,830,976 B2   9/2014   Farricker
(Continued)

OTHER PUBLICATIONS

Cisco Wireless Controller Configuration Guide, Release 8.0, https://www.cisco.com/c/en/us/td/docs/wireless/controller/8-0/configuration-guide/b_cg80.html#ID81, Accessed Sep. 16, 2019.
(Continued)

*Primary Examiner* — Pao Sinkantarakorn
*Assistant Examiner* — Kabir U Jahangir

(57) ABSTRACT

A medical device comprises a medical imaging, diagnostic, or therapeutic component (10), and an access point (30) operating as a hub for a wireless local area network (WLAN) complying with a wireless communication protocol having a defined set of WLAN channels. The access point includes a radio (32), an electronic processor (34), and a non-transitory storage medium (36) storing a list of one or more critical medical WLANs (40) and instructions executable by the electronic processor. Scan instructions (42) operate the radio to measure traffic on the WLAN channels generated by critical medical WLANs listed on the list (40). Channel selection instructions (44) select a channel based on at least the measured traffic on the WLAN channels generated by critical medical WLANs on the list (40). WLAN operating instructions (46) operate the access point as a hub for a medical device WLAN carrying traffic on the selected WLAN channel.

15 Claims, 2 Drawing Sheets

(51) Int. Cl.
*H04W 24/10* (2009.01)
*H04W 72/04* (2009.01)
*H04W 84/12* (2009.01)

(56) References Cited

U.S. PATENT DOCUMENTS

| | | |
|---|---|---|
| 9,084,267 B2 | 7/2015 | Farricker |
| 2002/0188723 A1* | 12/2002 | Choi ............... H04W 36/06 709/225 |
| 2006/0029023 A1* | 2/2006 | Cervello ............ H04W 72/02 370/333 |
| 2011/0134865 A1 | 6/2011 | Gaur |
| 2016/0287470 A1 | 10/2016 | Lewis et al. |

OTHER PUBLICATIONS

"Transforming Care Delivery", Philips, https://www.usa.philips.com/healthcare, Accessed Sep. 16, 2019.
International Search Report and Written Opinion, International Application No. PCT/EP2018/055994, dated May 24, 2018.

* cited by examiner

ACCESS POINT WITH LIFE-CRITICAL NETWORK AWARE IEEE 802.11 CHANNEL SELECTION

CROSS-REFERENCE TO PRIOR APPLICATIONS

This application is the U.S. National Phase application under 35 U.S.C. § 371 of International Application No. PCT/EP2018/055994, filed on 12 Mar. 2018, which claims the benefit of U.S. Provisional Patent Application No. 62/474,212, filed on 21 Mar. 2017. These applications are hereby incorporated by reference herein.

FIELD

The following relates generally to the wireless medical device arts, to medical devices with wireless networking capability, to the medical wireless local area network (medical WLAN) arts, to medical information technology (IT) arts, and related arts.

BACKGROUND

Wireless medical devices are sometimes deployed with wireless network capability for wireless interfacing with components, Electronic Medical Record (EMR) systems, and the like. In some such devices, the wireless networking hardware complies with the IEEE 802.11 specification for the media access control (MAC) and physical layers. Depending on the regulatory domain of the deployment and the RF bands enabled, the number of available channels can range from as few as three channels to a dozen or more channels. A given network is identified by its Service Set Identifier (SSID) so that traffic associated with the specific network is thereby identified. A medical device with wireless networking capability compliant with the IEEE 802.11 standard may include an access point (AP), i.e. hardware that acts as the communication hub. The AP establishes a network between two wireless devices, referred to herein as "stations" (one station may be the medical device itself), and endeavors to select an unused or lightly used channel for this network traffic.

As an illustrative example, the MobileDiagnost wDR™ mobile digital radiography (DR) device available from Koninklijke Philips N.V., Eindhoven, The Netherlands, is an example of a medical device having IEEE 802.11-compliant networking capability. This device is a mobile DR system which can be wheeled into a patient's hospital room or other location to acquire DR images. The images are recorded by a Skyplate™ wireless portable detector which is wirelessly read by the mobile DR system via an 802.11-compliant network established by the mobile DR system.

Such a wireless medical device competes with other bandwidth users, such as any WiFi or other IEEE 802.11-compliant wireless local area network (WLAN) in the vicinity. Under the IEEE 802.11 standard, each wireless network is identified by its Service Set Identifier (SSID) so that traffic associated with the specific network is thereby identified. A medical device with wireless networking capability compliant with the IEEE 802.11 standard may include an access point (AP), i.e. hardware that acts as the communication hub. The AP establishes a network between two wireless devices, referred to herein as "stations", and endeavors to select an unused or lightly used channel for this network traffic.

The following discloses new and improved apparatuses and methods.

SUMMARY

In one disclosed aspect, a medical device comprises a medical imaging, diagnostic, or therapeutic component, and an access point configured to operate as a hub for a wireless local area network (WLAN) complying with a wireless communication protocol and having a defined set of WLAN channels. The access point includes a radio, an electronic processor, and a non-transitory storage medium storing: a list of one or more critical medical WLANs; scan instructions readable and executable by the electronic processor to operate the radio to measure traffic on the WLAN channels generated by operation of critical medical WLANs listed on the list of one or more critical medical WLANs; channel selection instructions readable and executable by the electronic processor to select a WLAN channel based on at least the measured traffic on the WLAN channels generated by operation of critical medical WLANs; and WLAN operating instructions readable and executable by the electronic processor to operate the access point as a hub for a medical device WLAN carrying traffic on the WLAN channel selected by execution of the channel selection instructions.

In another disclosed aspect, a method is performed using an access point configured to operate as a hub for a wireless local area network (WLAN) complying with a wireless communication protocol and having a defined set of WLAN channels. The method comprises: storing a list of one or more critical medical WLANs in a non-transitory storage of the access point; using the access point to measure traffic on the WLAN channels generated by operation of critical medical WLANs listed on the list of one or more critical medical WLANs; selecting a WLAN channel based at least on the measured traffic on the WLAN channels generated by operation of critical medical WLANs; and using the access point to carry traffic between two or more wireless devices on the selected WLAN channel.

One advantage resides in providing for reduced interference by wireless medical devices with networking capability on wireless medical networks carrying patient vital sign data, therapeutic device communications, or other life-critical wireless traffic.

Another advantage resides in providing channel allocation with improved robustness for wireless medical devices with networking capability.

Another advantage resides in providing wireless medical devices with networking capability which have contextual channel selection capability.

Another advantage resides in providing improved wireless communication traffic diagnostics for wireless medical networks in hospitals or other medical facilities.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
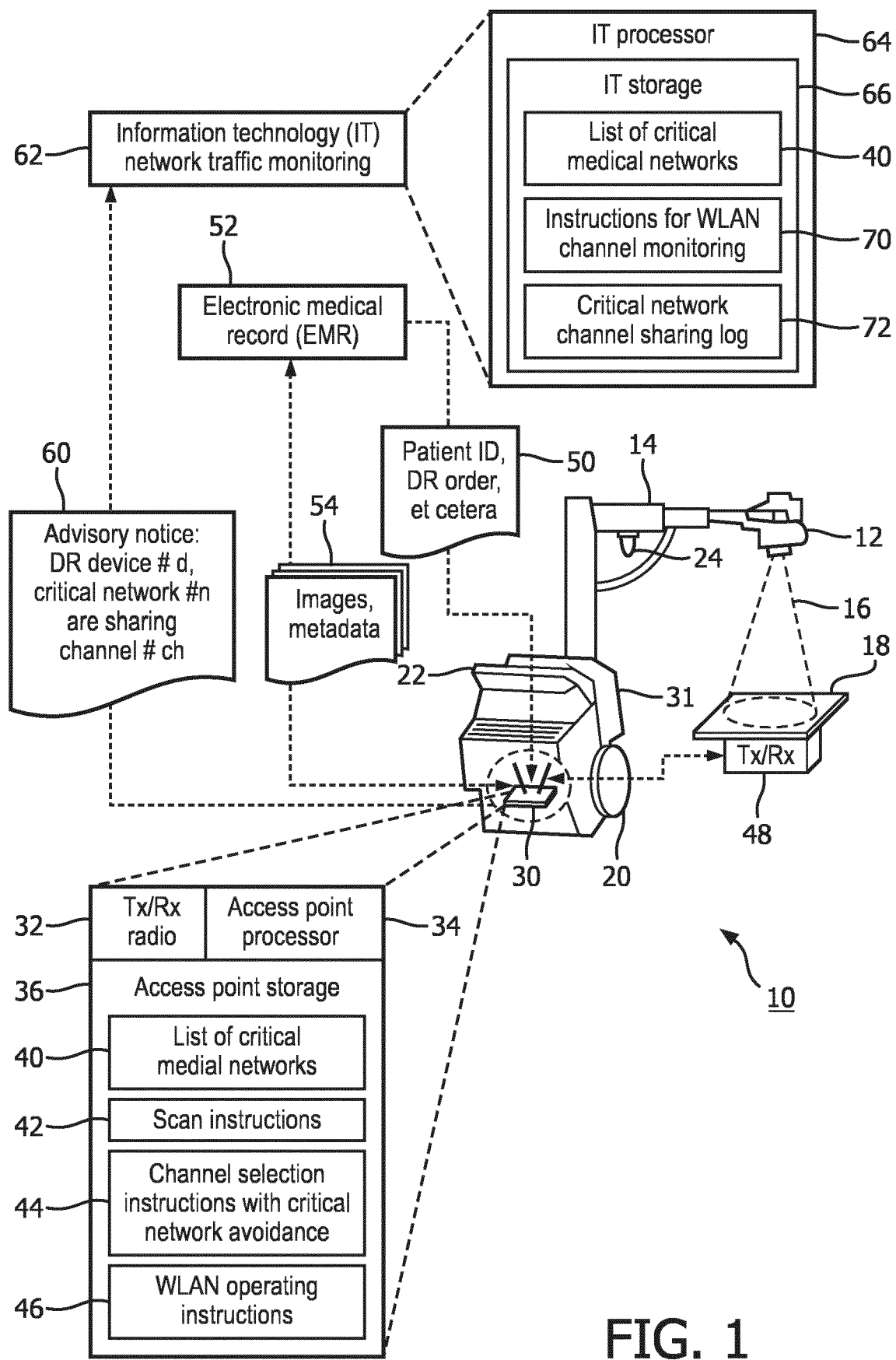
FIG. 1 diagrammatically shows an illustrative medical device comprising a mobile digital radiography (DR) device and contextual components including a wireless portable x-ray detector accessory and an Electronic Medical Record (EMR).

A wireless communication protocol such as IEEE 802.11 wireless communication protocol has a defined set of WLAN channels. For IEEE 802.11, the defined set of WLAN channels depends on the specific standard, e.g. 802.11b and 802.11g utilize a set of channels in the 2.400-2.500 GHz spectrum, while 802.11a and 802.11n utilize a set of channels in the 4.915-5.825 GHz band, with the specific channels designated by center frequency and bandwidth. The particular regulatory domain may also control the defined set of WLAN channels available for use by a WLAN. In a simple deployment (e.g., a home network), the WLAN channel for a network is chosen manually; however, this approach is impractical in a setting such as a hospital which includes a large number of WLANs that physically overlap in space and can therefore interfere with each other if they are allocated to a common channel. For such settings, automatic WLAN channel selection is performed, which selects the WLAN channel for a WLAN based on measurements of the channel traffic, e.g. quantified by metrics such as average signal level, average channel use as a fraction of time, measured noise, or a combination of such metrics.

It is recognized herein that such approaches may be non-optimal in a hospital or other medical setting. This is because the criticality of the WLANs present in the medical setting vary drastically. For example, Table 1 illustrates three WLANs of types typically found in hospitals. It will be appreciated that the WLAN identified by the Service Set Identifier (SSID) "PatientMonitoring" carries patient monitoring data which can be life-critical. More generally, a life-critical network is one for which a malfunction can lead to injury or death, or severe damage to equipment and/or the environment of the medical facility. As another example, a life-critical network may carry data for managing infusion pumps delivering fluids or drugs to patients. Any delay or loss of data on a life-critical WLAN can have serious consequences. By contrast, the WLAN identified by SSID="Guest" carries data of much lower criticality, and delays or loss of data on the "Guest" WLAN is of much less consequence. However, existing channel selection approaches generally do not take into account the criticality of the WLANs. Because of this, by way of non-limiting illustration, the channel selection process may choose a WLAN channel carrying traffic of the critical "PatientMonitoring" WLAN if this traffic is light, thus increasing likelihood of a serious delay or loss of potentially life-critical patient data transmission.

point that is selecting a channel for a WLAN; however, it is of especial value in the context of mobile medical devices that may be deployed in various hospital rooms or other areas of a hospital and are required to set up a WLAN for supporting the mobile medical device.

In one illustrative approach, the list of one or more critical medical networks (e.g. identified by SSIDs in an IEEE 802.11-compliant WLAN framework) is used to avoid selecting a channel carrying traffic of a critical medical network. The list of one or more critical medical networks is suitably manually curated by an information technology (IT) professional, e.g. using a Graphical User Interface (GUI) menu. Optionally, each SSID could also have a signal maximum signal level threshold (dB) that could also be considered. A scan routine measures traffic on the set of WLAN channels available under the wireless communication protocol. In an IEEE 802.11 context, this scan may use IEEE 802.11 broadcast probe requests to determine which SSIDs are operating on a particular WLAN channel. This creates a scan list, i.e. a list of WLAN radio channels and the networks operating on each channel (e.g., identified by SSID). If a life-critical network is a hidden network that does not respond to broadcast probe requests, directed probe requests can also be used to find such a life-critical network. A WLAN radio channel selection routine then creates a candidate WLAN channel list, and in so doing excludes WLAN radio channels where life-critical networks have been measured above a certain signal level. The WLAN channel list may be ranked by or use other criteria such as noise and WLAN radio channel usage to further refine the radio channel list. A WLAN radio channel is selected from the candidate list, or alternatively the list is displayed and a user selects a radio channel from the list. If the candidate WLAN radio channel list is empty and a radio channel with a life-critical network must be selected, then an advisory notice is optionally transmitted to the IT channel monitoring system for review by an IT professional and/or logging in a WLAN channel usage log.

With reference to FIG. 1, an illustrative example of a mobile medical device is a digital radiography (DR) device 10 which includes an x-ray source 12, e.g. an x-ray tube

TABLE 1

| Network Name (SSID) | WLAN Channel Set | Purpose | Criticality | Average Channel Use For SSID Across All APs |
|---|---|---|---|---|
| "PatientMonitoring" | 5 GHz US non-DFS channels (36, 40, 44, 48, 149, 153, 157, 161 & 165) | Real-time patient monitoring | High (life critical) | 20% |
| "Staff" | 5 GHz US including DFS and non-DFS channels (36, 40, 44, 48, 52, 56, 60, 64, 100, 104, 108, 112, 116, 149, 153, 157, 161 & 165) | Staff activities (email, hospital applications, remote surveillance, etc) | Medium (mission critical) | 25% |
| "Guest" | 2.4 GHz US channels (1, 2, 3, 4, 5, 6, 7, 8, 9, 10, 11, 12) | Visitor support (email, web browsing, streaming video, etc) | Low | 30% |

In the SSID="Staff" network, to free RF spectrum, DFS channels may be used in areas where only the hospital staff is allowed (i.e. offices, labs, etc. . . . ).

In embodiments disclosed herein, the channel selection is modified to take into account the criticality of network traffic in a medical setting. To this end, a list of one or more critical medical networks is maintained, and this information is taken into account during channel selection. Such an approach is useful in any medical setting and for any access mounted on a robotic arm 14 to facilitate flexible positioning respective to a patient undergoing DR imaging. The DR device 10 is programmed to generate an x-ray beam 16 (diagrammatically indicated in FIG. 1) that transmits through a patient (not shown) and is detected by a wireless x-ray detector 18. The illustrative DR device 10 is a mobile device, and includes wheels 20 and a handle 22 for rolling transport between hospital rooms or the like. As a non-limiting illustrative example, one mobile DR device of this type is the MobileDiagnost wDR™ mobile digital radiography (DR) device available from Koninklijke Philips N.V., Eindhoven, The Netherlands, which uses a Skyplate™ wireless portable detector as the wireless x-ray detector 18. The use of the x-ray source 12 mounted on the robotic arm 14 in combination with the wireless x-ray detector 18 provides medical personnel with substantial flexibility in the positioning of the x-ray source and detector for imaging a specific anatomical region of a patient. The DR device 10 may include other features known in the art, such as a warning lamp 24 that is illuminated whenever the x-ray source 12 is outputting the x-ray beam 16 to warn medical personnel and others in the area of the potential radiation exposure hazard.

The DR device 10 is the illustrative medical device. More generally, the medical device may be any medical imaging, diagnostic, or therapeutic component, e.g. another type of imaging device such as a portable ultrasound (US) system (e.g. with wireless communication to an US probe); a diagnostic device such as an electronic electrocardiograph (ECG); a therapeutic device such as a radiation therapy delivery device; and/or so forth. A medical device can incorporate a separate WLAN network for various reasons, e.g. to communicate wirelessly between components of the device. WLAN has certain advantages for providing wireless communication in a medical device context, e.g. relatively large data handling capacity. However, newer IEEE 802.11 standards and draft standards that allow higher through-put, such as IEEE 802.11ac, 80211ax, also have a higher potential to disrupt traffic as they transmit data across multiple channels. The disclosed approaches for avoiding or at least reducing the impact of a WLAN set up by such a medical device on critical medical WLANs is useful in the case of any medical device that deploys WLAN in support of device operations; however, it is of especial use in the case of mobile or portable medical devices that frequently deploy a newly created WLAN, e.g. each time the illustrative DR device 10 is wheeled into a hospital room to perform DR imaging of a patient, it may be expected to deploy a new WLAN in support of that DR imaging session. Due to its mobility, the DR device 10 can be expected to be deployed in a wide range of locations throughout the hospital, thus potentially presenting a wide range of possibilities for interference with critical medical networks. The disclosed improvements substantially reduce, or even in some instances eliminate, the possibility of such interference.

With continuing reference to FIG. 1, the illustrative DR device 10 includes an access point 30, which is diagrammatically shown in FIG. 1 as a discrete device including two antennae but which more generally may have substantially any form factor, and is preferably integrated into the DR device 10, e.g. contained in a housing 31 that also contains or supports the operational digital radiography component. The access point 30 is diagrammatically expanded in the lower left of FIG. 1 to illustrate components of the access point 30, including a transceiver (i.e. transmit/receive or Tx/Rx) radio 32, an electronic processor 34, and a non-transitory storage medium 36, e.g. a flash memory, solid state drive (SSD) or other electronic storage medium; a hard disk or other magnetic storage medium; various combinations thereof; or so forth. The radio 32 is tuned to transmit over the operational bandwidth of a wireless communication protocol having a defined set of WLAN channels. For example, IEEE 802.11b and 802.11g transmit over a set of channels in the 2.400-2.500 GHz spectrum; whereas, IEEE 802.11a transmits over the 4.915-5.825 GHz band. These are merely non-limiting illustrative examples. The electronic processor 34 reads and executes instructions stored in the non-transitory storage medium 36 to perform tasks such as operating the radio 32 in compliance with the chosen 802.11 or other wireless communication protocol.

More particularly, the illustrative non-transitory storage medium 36 stores a list of one or more critical medical networks 40 and instructions readable and executable by the electronic processor 34 including: scan instructions 42; channel selection instructions 44 with life-critical networks avoidance; and WLAN operating instructions 46. The list of one or more critical medical networks 40 is suitably curated by IT professionals and preferably lists WLANs carrying patient data, therapeutic device operational or monitoring data, or other life-critical data. By way of non-limiting illustration, the list 40 may include the SSID="PatientMonitoring" WLAN of Table 1. The list of one or more critical medical networks 40 may, in some embodiments, list as few as a single critical medical network, e.g. if all life-critical data are communicated over a single patient monitoring network or the like. More typically, the list of one or more critical medical networks 40 lists a number of critical medical networks, e.g. maintained by different departments (e.g., cardiology, neonatal care, Intensive Care Units, and/or so forth) and/or for different purposes (e.g., a patient monitoring WLAN, a radiology WLAN, and/or so forth).

The instructions 42, 44, 46 executable by the electronic processor 34 of the access point 30 perform various operations. The scan instructions 42 are readable and executable by the electronic processor 34 to operate the radio 32 to measure traffic on the WLAN channels generated by operation of critical medical WLANs listed on the list 42 of one or more critical medical WLANs. Preferably, the scan instructions 42 are readable and executable by the electronic processor 34 to operate the radio 32 to measure total traffic on the WLAN channels as well, and perhaps to measure other information such as channel noise. The output of execution of the scan instructions may be used for various purposes; in the illustrative examples the output of execution of the scan instructions serves as input to the channel selection instructions 44, which are readable and executable by the electronic processor 34 to select a WLAN channel based on at least the measured traffic on the WLAN channels generated by operation of critical medical WLANs. More preferably, the channel selection instructions 44 are preferably readable and executable by the electronic processor 34 to select a WLAN channel based on both the measured total traffic on the WLAN channels and the measured traffic on the WLAN channels generated by operation of critical medical WLANs. The WLAN operating instructions 46 are readable and executable by the electronic processor 34 to operate the access point 30 as a hub for a medical device WLAN carrying traffic between two or more wireless devices on the WLAN channel selected by execution of the channel selection instructions 44. By way of non-limiting illustration, the medical device WLAN may carry traffic in the form of DR images captured by the wireless x-ray detector 18 and transmitted from the wireless x-ray detector 18 to the DR device 10 on the WLAN channel selected by execution of the channel selection instructions 44. This is indicated diagrammatically in FIG. 1 by the diagrammatic Tx/Rx radio 48 of the wireless x-ray detector 18 and a dotted connecting double-arrowhead line. The WLAN operating instructions 46 operate conventionally in accordance with the chosen wireless communication protocol, e.g. the chosen IEEE 802.11 protocol in illustrative examples, to transmit data packets with SSID headers and other headers and other associated packet metadata as appropriate for the chosen wireless communication protocol. In these hub operations, the access point 30 serves as a relay, i.e. receives data packets from the transmitting wireless device (e.g. the wireless x-ray detector 18 when sending DR images) and re-transmits the data packets to the receiving wireless device (e.g. the DR device 10 in the illustrative example; in some embodiments when the DR device 10 which hosts the access point 30 is one of the end-points no corresponding radio transmission is performed but rather the data are directly communicated between the access point 30 and the DR device 10 via an internal data bus or the like).

The access point 30 may also provide other wireless connectivity, optionally using other WLANs besides the medical device WLAN set up by the access point 30 itself. For example, the access point 30 may connect with a medical records WLAN to retrieve patient information 50 (e.g. patient identification, PID; a DR examination order; et cetera) from an electronic medical record (EMR) 52 (e.g. hosted on a server computer). Likewise, the access point 30 may connect with the medical records WLAN to send the DR images (and optionally associated metadata) 54 from the DR device 10 to the EMR 52.

In the following, some illustrative examples of medical device WLAN setup caused to be performed by the access point 30 by the electronic processor 34 reading and executing the instructions 42, 44 are described.

In one illustrative example, the channel selection instructions 44 include instructions readable and executable by the electronic processor 34 to: identify one or more channels with no measured traffic generated by operation of critical medical WLANs listed in the list 40; and select the WLAN channel for the medical device WLAN as the channel with lowest measured total traffic selected from the one or more channels with no measured traffic generated by operation of critical medical WLANs.

In another example, this is not possible because there are no WLAN channels that have no measured traffic generated by operation of critical medical WLANs (as measured by execution of the scan instructions 42). In this case, the channel selection instructions 44 may suitably further include instructions readable and executable by the electronic processor 34 to select the WLAN channel for the medical device WLAN as the channel with lowest measured total traffic, conditional on every channel having measured traffic generated by operation of critical medical WLANs.

In a variant embodiment, the channel selection instructions 44 may suitably further include instructions readable and executable by the electronic processor 34 to select the WLAN channel for the medical device WLAN as the channel with lowest measured total traffic and traffic generated by operation of critical medical WLANs below a threshold level, again conditional on every channel having measured traffic generated by operation of critical medical WLANs.

With continuing reference to FIG. 1, in some embodiments the channel selection instructions 44 include instructions readable and executable by the electronic processor 34 to one of: (1) select a WLAN channel with no measured traffic generated by operation of critical medical WLANs listed in the list 40 (if possible); or (2) operate the radio 32 to transmit an advisory notice 60 if every channel has measured traffic generated by operation of critical medical WLANs in the list 40. The advisory notice 60 may, for example, be transmitted to an information technology (IT) network traffic monitoring system 62, e.g. running on a server computer. The advisory notice 60 may be displayed on a display (not shown), logged in a network usage log, or otherwise utilized to inform IT personnel or field service engineers of the conflict between the medical device WLAN and a life-critical medical network.

In some embodiments, the list 40 of one or more critical medical WLANs includes a criticality measure associated with each critical medical WLAN. In such embodiments, the channel selection instructions 44 are suitably readable and executable by the electronic processor 34 to select the WLAN channel based on at least the measured traffic on the WLAN channels generated by operation of critical medical WLANs (as measured by execution of the scan instructions 42) and the criticality measures associated with the critical medical WLANs for which traffic is measured. For example, if every WLAN channel has measured traffic generated by operation of critical medical WLANs (as measured by execution of the scan instructions 42), then the WLAN channel for the medical device WLAN may be selected as a WLAN channel that is carrying only measured traffic generated by operation of a critical medical WLAN having a low criticality measure associated with it in the list 40. In other words, since a channel carrying traffic generated by operation of a critical medical WLAN must be selected, this approach selects a channel carrying traffic generated by operation of the "least critical" of the critical medical WLANs.

In the foregoing examples, the list 40 of critical medical networks is used by the access point 30 of the medical device 10 in order to avoid (to the extent possible) setting up the medical device WLAN on a channel that is already carrying traffic generated by operation of a critical medical WLAN (identified as such by being on the list 40). As already noted, in this setup process, if a channel carrying traffic generated by operation of critical medical WLAN cannot be avoided, then the advisory notice 60 may be transmitted.

With continuing reference to FIG. 1, additionally or alternatively the IT network traffic monitoring system 62 may perform such monitoring directly. To this end, the illustrative IT network traffic monitoring system 62 includes an electronic processor 64 and non-transitory storage medium 66 (e.g. a hard drive, SSD, RAID drive system, et cetera). The non-transitory storage medium 66 stores the list of critical medical networks 40, and also stores instructions 70 readable and executable by the electronic processor 64 to perform a WLAN channels monitoring process that monitors channel usage at all access points (including the access point 30 of the medical device 10 but also including all other access points serving as hubs for the various WLANs of the hospital). The WLAN channels monitoring process performed by execution of the instructions 70 also references the list of critical medical networks 40 to detect instances when a life-critical network is sharing a WLAN channel with some other WLAN (e.g. the medical device WLAN maintained by the access point 30 of the medical device 10). Such instances of sharing are logged in a life-critical network sharing log 72 stored on the IT non-transitory storage medium 66.

Figure 2:
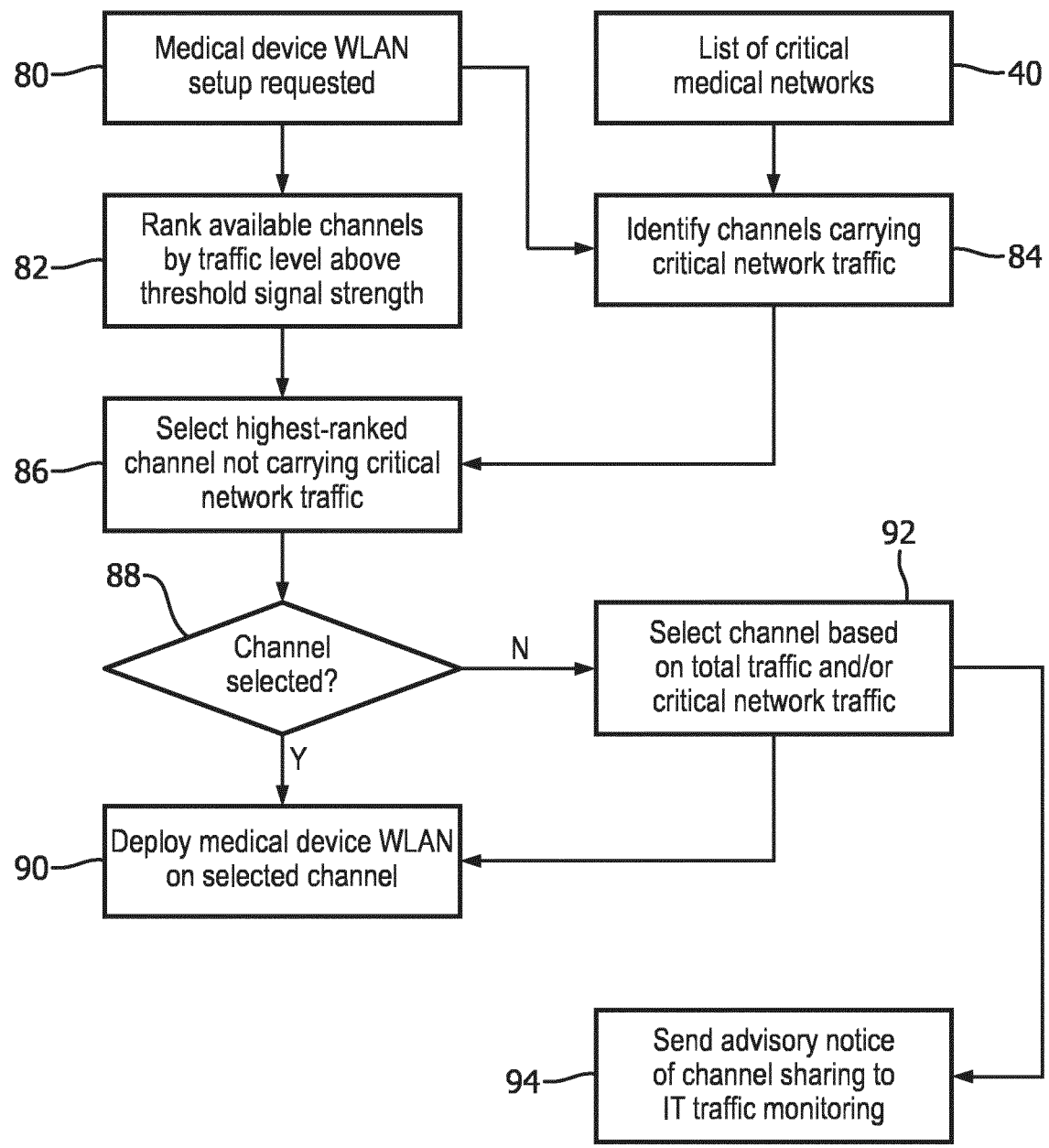
FIG. 2 diagrammatically flow charts a channel selection process suitably performed by the DR device of FIG. 1 during setup of a wireless network.

With reference to FIG. 2, a process suitably performed by the access point 30 executing the instructions 42, 44 is described. In an operation 80, a request for setup of a medical device WLAN is received by the access point 30, e.g. from the electronic processor of the DR device 10. (The actual network setup is performed by the access point 30). In an operation 82, the scan instructions 42 are run and the channel selection instructions 44 are run to rank the available channels by traffic level (optionally above a chosen threshold signal strength to avoid barring channels carrying distant traffic with which interference is unlikely). Additionally, in an operation 84 performed by the running channel selection instructions 44, the list of critical medical networks 40 is referenced to identify the channels carrying traffic generated by operation of critical medical WLANs. This identification is suitably done by comparing the SSIDs in the list 40 against the SSID information in the WLAN message headers. In an operation 86 performed by the running channel selection instructions 44, the highest-ranked channel that is not carrying traffic generated by operation of a critical medical WLAN is selected, if possible. In an operation 88, if such a channel was able to be selected then it is designated as the selected WLAN channel for the medical device WLAN, which is then deployed on the selected WLAN channel in an operation 90.

On the other hand, if in the decision 88 it is recognized that no channel is available that is not carrying traffic generated by operation of a critical medical WLAN (or, put another way, every WLAN channel is carrying traffic generated by operation of a critical medical WLAN), then in an operation 92 a channel is selected on some other basis, e.g. selecting the channel with the least total traffic, optionally further based on minimizing the amount of traffic generated by operation of a critical medical WLAN. In such a case, in an optional operation 92 the advisory notice 60 (see FIG. 1) is transmitted.

Some IEEE 802.11 protocols, such as 802.11n and 802.11ac, allow for the use of channel bonding, in which an access point can have one or more secondary channels that can be bonded to the primary channel to transfer at higher data rates. These secondary channels can be taken into account when selecting a channel to operate on as per operations 86, 92. For example, in 802.11 modes in which secondary channels are the same as critical access points, one mitigation would be for the access point to disable channel-bonding. In the operation 94, the advisory notice 60 can include identification of whether the channel sharing is the primary or secondary channel.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical device, comprising:
a mobile medical imaging, diagnostic, or therapeutic component; and
an access point configured to operate as a hub for a wireless local area network (WLAN) complying with a wireless communication protocol and having a defined set of WLAN channels, the access point including a radio, an electronic processor, and a non-transitory storage medium storing:
a list of one or more critical medical WLANs carrying life-critical patient monitoring data;
scan instructions readable and executable by the electronic processor to operate the radio to measure total traffic on the WLAN channels and traffic on the WLAN channels generated by operation of critical medical WLANs listed on the list of one or more critical medical WLANs;
channel selection instructions readable and executable by the electronic processor to select a WLAN channel based on at least both the measured total traffic on the WLAN channels and the measured traffic on the WLAN channels generated by operation of critical medical WLANs; and
WLAN operating instructions readable and executable by the electronic processor to operate the access point as a hub for a medical device WLAN carrying traffic on the WLAN channel selected by execution of the channel selection instructions from a detector to the mobile medical imaging, diagnostic, or therapeutic component.

2. The medical device of claim 1, wherein the channel selection instructions include:
instructions readable and executable by the electronic processor to:
identify one or more channels with no measured traffic generated by operation of critical medical WLANs, and
select the WLAN channel as the channel with lowest measured total traffic selected from the one or more channels with no measured traffic generated by operation of critical medical WLANs.

3. The medical device of claim 2, wherein the channel selection instructions further include:
instructions readable and executable by the electronic processor to select the WLAN channel as the channel with lowest measured total traffic conditional on every channel having measured traffic generated by operation of critical medical WLANs.

4. The medical device of claim 2, wherein the channel selection instructions further include:
instructions readable and executable by the electronic processor to select the WLAN channel as the channel with lowest measured total traffic and traffic generated by operation of critical medical WLANs below a threshold level conditional on every channel having measured traffic generated by operation of critical medical WLANs.

5. The medical device of claim 1, wherein the channel selection instructions include:
instructions readable and executable by the electronic processor to one of:
select a WLAN channel with no measured traffic generated by operation of critical medical WLANs; or
operate the radio to transmit an advisory notice if every channel has measured traffic generated by operation of critical medical WLANs.

6. The medical device of claim 1, wherein:
the list of one or more critical medical WLANs includes a criticality measure associated with each critical medical WLAN; and
the channel selection instructions are readable and executable by the electronic processor to select the WLAN channel based on at least the measured traffic on the WLAN channels generated by operation of critical medical WLANs and the criticality measures associated with the critical medical WLANs for which traffic is measured such that a least critical WLAN channel is selected.

7. The medical device of claim 1, further comprising:
a housing containing or supporting both the medical imaging, diagnostic, or therapeutic component and the access point.

8. A medical device, comprising:
a medical imaging, diagnostic, or therapeutic component; and
an access point configured to operate as a hub for a wireless local area network (WLAN) complying with a wireless communication protocol and having a defined set of WLAN channels, the access point including a radio, an electronic processor, and a non-transitory storage medium storing:
- a list of one or more critical medical WLANs;
- scan instructions readable and executable by the electronic processor to operate the radio to measure total traffic on the WLAN channels and traffic on the WLAN channels generated by operation of critical medical WLANs listed on the list of one or more critical medical WLANs;
- channel selection instructions readable and executable by the electronic processor to select a WLAN channel based on at least both the measured total traffic on the WLAN channels and the measured traffic on the WLAN channels generated by operation of critical medical WLANs; and
- WLAN operating instructions readable and executable by the electronic processor to operate the access point as a hub for a medical device WLAN carrying traffic on the WLAN channel selected by execution of the channel selection instructions;
- wherein the medical imaging, diagnostic, or therapeutic component comprises a mobile digital radiography (DR) device programmed to output an x-ray beam and to cause the access point to operate as a hub for the medical device WLAN carrying a DR image from a wireless x-ray detector to the mobile DR device.

9. A method performed using an access point configured to operate as a hub for a wireless local area network (WLAN) complying with a wireless communication protocol and having a defined set of WLAN channels, the method comprising:
- storing a list of one or more critical medical WLANs carrying life-critical patient monitoring data in a non-transitory storage of the access point;
- using the access point, measuring a total traffic on the WLAN channels and traffic on the WLAN channels generated by operation of critical medical WLANs listed on the list of one or more critical medical WLANs;
- selecting a WLAN channel based at least on the measured total traffic on the WLAN channels and the measured traffic on the WLAN channels generated by operation of critical medical WLANs; and
- using the access point, carrying traffic between a detector and a mobile imaging, diagnostic, or therapeutic component on the selected WLAN channel.

10. The method of claim 9, wherein the selecting of the WLAN channel includes:
- identifying one or more channels with no measured traffic generated by operation of critical medical WLAN; and
- selecting the WLAN channel as the channel with lowest measured total traffic selected from the one or more channels with no measured traffic generated by operation of critical medical WLANs.

11. The method of claim 10, wherein the selecting of the WLAN channel includes:
- determining that each of the WLAN channels has measured traffic generated by operation of critical medical WLANs; and
- selecting the WLAN channel as the channel with lowest measured total traffic.

12. The method of claim 10, wherein the selecting of the WLAN channel includes:
- determining that each of the WLAN channels has measured traffic generated by operation of critical medical WLANs; and
- selecting the WLAN channel as the channel with lowest measured total traffic and with traffic generated by operation of critical medical WLANs below a threshold level.

13. The method of claim 9, wherein:
- the storing of the list of one or more critical medical WLANs includes storing a criticality measure associated with each critical medical WLAN; and
- the selecting of the WLAN channel is based on at least the measured traffic on the WLAN channels generated by operation of critical medical WLANs and the criticality measures associated with the critical medical WLANs for which traffic is measured such that a least critical WLAN channel is selected.

14. The method of claim 9, further comprising:
operating a medical device to acquire medical imaging, diagnostic, or therapeutic data including using the access point to carry traffic from an accessory device to the medical device on the selected WLAN channel.

15. The method of claim 9, further comprising:
operating a mobile digital radiography (DR) device to transmit an x-ray beam; and
using the access point to carry a DR image from a wireless x-ray detector to the mobile DR device on the selected WLAN channel.

* * * * *